(12) United States Patent
Quinn

(10) Patent No.: US 6,942,638 B1
(45) Date of Patent: Sep. 13, 2005

(54) NEEDLELESS INJECTOR AND AMPULE SYSTEM

(76) Inventor: Kerry Quinn, 1879 Morris Ct., Erie, CO (US) 80516

(*) Notice: Subject to any disclaimer, the term of this patent is extended or adjusted under 35 U.S.C. 154(b) by 325 days.

(21) Appl. No.: 10/159,853

(22) Filed: May 30, 2002

(51) Int. Cl.⁷ .......................... A61M 5/30; A61M 5/315
(52) U.S. Cl. ........................................ 604/68; 604/222
(58) Field of Search .................... 604/19, 48, 500, 604/506, 507, 511, 68–72, 93.01, 181, 187, 604/218–222, 230

(56) References Cited

U.S. PATENT DOCUMENTS

| 2,704,542 A | * | 3/1955 | Scherer ..................... 604/506 |
| 2,704,543 A | * | 3/1955 | Scherer ....................... 604/68 |
| 3,335,722 A | * | 8/1967 | Lowry et al. ................. 604/69 |
| 3,424,154 A | * | 1/1969 | Kinsley ........................ 604/70 |
| 3,540,444 A | * | 11/1970 | Moreland ..................... 604/72 |
| 4,124,024 A | * | 11/1978 | Schwebel et al. ............. 604/69 |
| 5,312,335 A | * | 5/1994 | McKinnon et al. ........... 604/72 |
| 5,397,313 A | * | 3/1995 | Gross ......................... 604/218 |
| 5,620,423 A | * | 4/1997 | Eykmann et al. ........... 604/219 |
| 5,865,795 A | | 2/1999 | Schiff et al. |
| 6,053,895 A | * | 4/2000 | Kolberg et al. ............. 604/218 |
| 6,398,763 B1 | * | 6/2002 | Richardson et al. ........ 604/218 |
| 2002/0022806 A1 | * | 2/2002 | Witowski .................... 604/221 |

* cited by examiner

*Primary Examiner*—Nicholas D. Lucchesi
*Assistant Examiner*—Mark K. Han
(74) *Attorney, Agent, or Firm*—Ramon L. Pizarro; Edwin H. Crabtree

(57) ABSTRACT

A needle-less injection system that uses an ampule with an elongated hollow body. The elongated hollow body including a nozzle and an aperture for accepting a plunger, the aperture for accepting a plunger extends from the second end towards the first end and is in fluid communication with the nozzle. The ampule cooperates with a generally cylindrical plunger. The plunger includes a first end and a second end, and a concave rib. The concave rib is extends about the perimeter of the plunger and extends towards the first end of the plunger.

16 Claims, 5 Drawing Sheets

NEEDLELESS INJECTOR AND AMPULE SYSTEM

BACKGROUND OF THE INVENTION (a) Field of the Invention

This invention generally relates to a system for the subcutaneous delivery of medicaments, and more particularly to a hand held actuator, and a plunger and ampule or vial used to deliver a stream of medication.

(b) Discussion of Known Art

The need for a needle-less injection device that can be used to deliver a fine, high-pressure stream of medication through the skin has been recognized for some time. However, the problems associated with creating this high-pressure stream, particularly with a self-contained, hand-held device, has proven to be a greater challenge than expected. The typical approach at creating these streams has been to use a piston that is driven by a CO2 cartridge, compressed air, or a spring. The piston is then used to drive the medicament from a reservoir through a small nozzle that is used to create the fine stream that is to penetrate the skin. The size and energy of the stream allows the stream to penetrate the skin to a depth where it can then be absorbed by the body.

One important problem is the creation of such a stream is the creation of a nozzle that provides a tight, uniform stream, and not a spray of the embodiment.

Another important problem associated with the design of a needle-less injection system involves the efficient delivery of the dose of medicament held within the reservoir. In other words, it is important that the system does not allow medicament to escape between the piston and the reservoir or cylinder through which the medicament is being delivered. The problem of loss of the medicament is typically caused by the escape of medicament under the pressure required to adequately deliver the medicament through the nozzle.

Still another important problem associated with needle-less injection devices, and particularly with hand-held devices of this type, is the provision of sufficient power to create and deliver a stream with sufficient energy so that the stream can penetrate the body to a depth where the medicament can be absorbed.

Yet another problem associated with needle-less devices is maintenance of a required amount of pressure during the delivery of the medicament from the reservoir, through the nozzle.

SUMMARY

It has been discovered that the problems left unanswered by known art can be solved by providing a needleless injection device including:

An ampule, the ampule including an elongated hollow body, the elongated hollow body having a first end and a second end, the first end of the hollow body including a nozzle, and the second end of the hollow body including an aperture for accepting a plunger, the aperture for accepting a plunger extending from the second end towards the first end and being in fluid communication with the nozzle; and A generally cylindrical plunger, the plunger including a first end and a second end, the plunger also including a concave rib extending about the perimeter of the plunger and extending towards the first end.

According to one example of the invention the body of the plunger is centered about an axis and first end of the plunger includes a generally conical end that is centered about the axis. Additionally, the conical end will extend from the concave portion of the concave rib. Still further, it is contemplated that the plunger will include a second rib, the second rib being between the concave rib and the second end of the plunger.

It is contemplated that the plunger will fit into the aperture in the ampule, with the concave rib sealingly engaging the sidewalls of the aperture in the body of the ampule. The second rib will also cooperate with the sidewalls of the aperture of the ampule and may provide some sealing function, but will primarily serve to stabilize or align the plunger as it is forced through the ampule.

The ampule will be connected to an actuator that will provide the power to push the plunger through the ampule and drive the medicament from the ampule through the nozzle. In an illustrated example of the actuator, the actuator includes a casing that holds a spring that is used to drive a rod. The rod in-turn pushes against the plunger, which then pushes the medicament through the ampule.

The release of the spring in the actuator is accomplished by providing a hammer that includes a forward end that is adapted for cooperating with the rod and the trigger mechanism, and an aft end that is adapted for cooperating with the spring. The trigger mechanism is used to retain the spring in a loaded or compressed position, and then release the spring to drive the plunger through the ampule.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
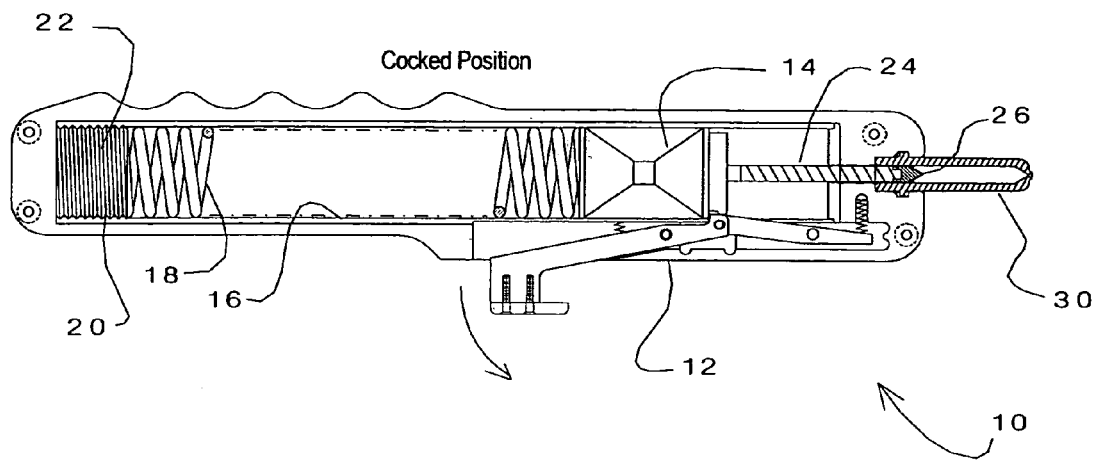
FIG. 1 is a plan view of the system in the cocked position. The view is a cut-away view with the cover of the actuator removed and sections of the internal sleeve removed, so that the internal components may be observed.

Turning now to FIG. 1, where a needle-less injection system 10 using principles taught herein has been illustrated, it will be understood that it is contemplated that the system may be used with a hand held actuator 12 or other actuator, such as using a pneumatic piston or combustion driven piston. In the illustrated example, the hand held actuator 12 includes a hammer 14 that slides along a sleeve 16. The hammer 14 is powered by a spring 18 that is held within the sleeve 16. The power or driving force provided by the spring 18 may fixed by creating a device that will allow the spring 18 to be compressed a set distance or by providing a spring compression adjustment mechanism 20, such as the threaded plug 22 that is mounted on an end of the sleeve 16.

Figure 2:
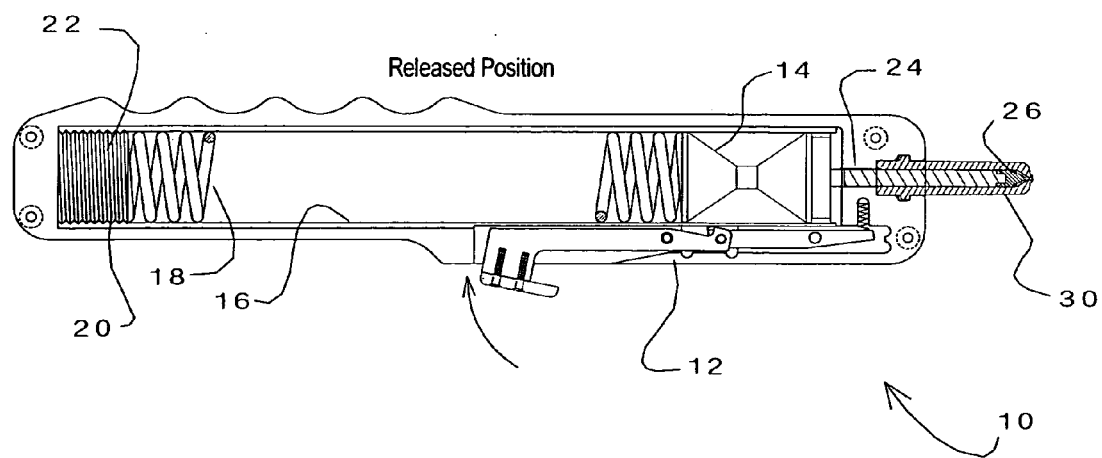
FIG. 2 is a plan view of the system in the fired position. The view is a cut-away view with the cover of the actuator removed and sections of the internal sleeve removed, so that the internal components may be observed.
Figure 3:
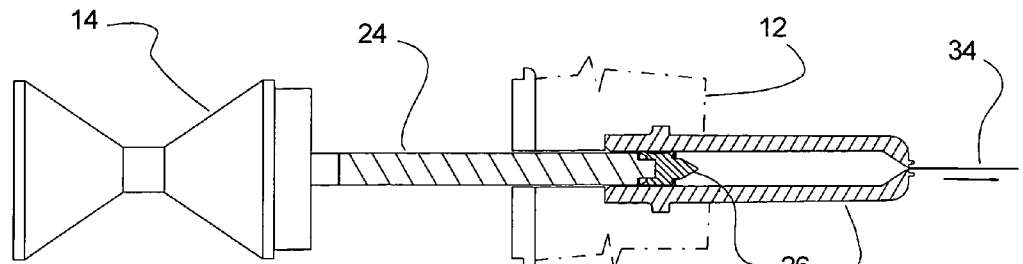
FIG. 3 is cut-away view illustrating the cooperation of the hammer, the push-rod, the vial or ampule and the seal.

As shown on FIGS. 1 and 2, energy is stored in the spring 18 by compressing the spring 18 to the "cocked position" illustrated in FIG. 1. This energy is then released to the hammer 14, which drives a rod 24 that extends between the hammer 14 and a plunger 26. The plunger 26 fits into and seals an aperture 28 in an ampule 30. The ampule 30 is attached to the actuator 12 by way of a bayonet connector 32, or a threaded connector, or any other suitable connector.

Turning to FIGS. 2–6 it will be understood that the disclosed system will deliver medicament through the skin by creating a very thin, high energy or velocity, jet of medicament 34 through the ampule 30. The jet of medicament 34 is produced by driving the plunger 26 through the aperture 28 to pressurize the fluid medicament 36 in the ampule 30, which pushes the medicament 36 through a nozzle 38 located on the second end 50 of the ampule 30.

It is contemplated that the ampule 30 will be made from a readily moldable material, such as a pharmaceutical grade polypropylene material that is suitable for injection molding or other polymer that is suitable for injection molding. An important drawback to the use of polymers as the material for the ampule 30 is that the mechanical properties of these materials allow these materials to deflect under the pressures needed for creating the jet of medicament 34 through the nozzle 38. Additionally, fabrication of the ampule 30 from stiffer materials results in a device that is too brittle or a device that cannot be manufactured through the use of high production rate methods, such as injection molding. Therefore, the machining of the ampules from stainless steel would be a prohibitively expensive approach at manufacturing the device. Furthermore, an opaque material will not allow the user of the device to ascertain whether the plunger 26 has traveled through the desired length of the ampule 30, and delivered the adequate dosage of medicament.

Figure 4:
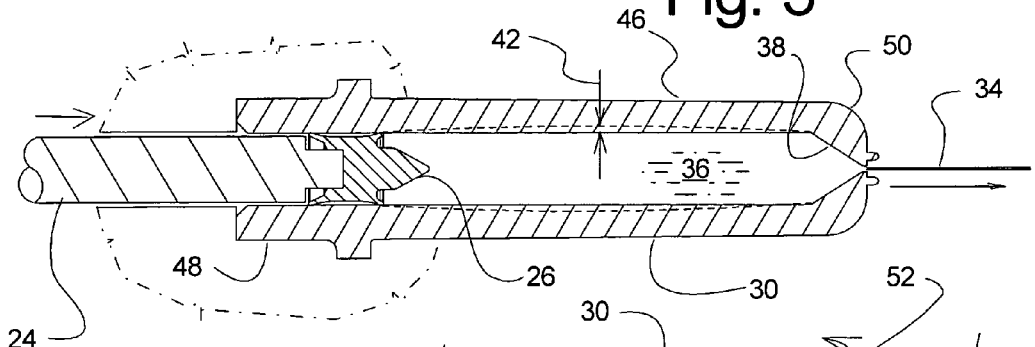
FIG. 4 is an enlarged view of components shown in FIG. 3, and illustrates the problem of deflection of the sidewalls of the vial or ampule while the plunger or seal is driven towards the nozzle to force the medicament from the ampule.
Figure 5:
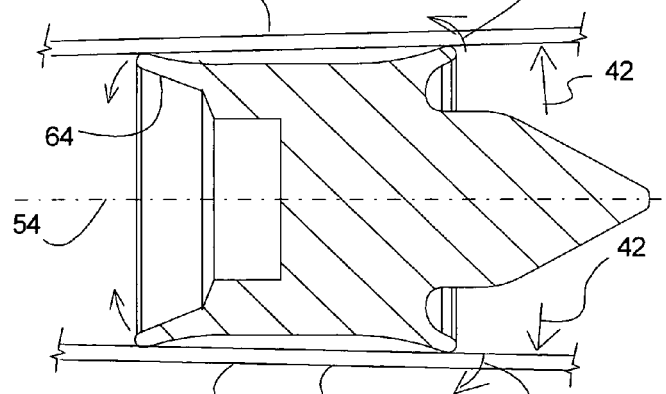
FIG. 5 is a close-up, sectional view of the seal or plunger as it is driven through the vial or ampule. The view illustrates the deformation of the vial or ampule and the deflection of the plunger to compensate for the dimensional changes in the ampule.
Figure 6:
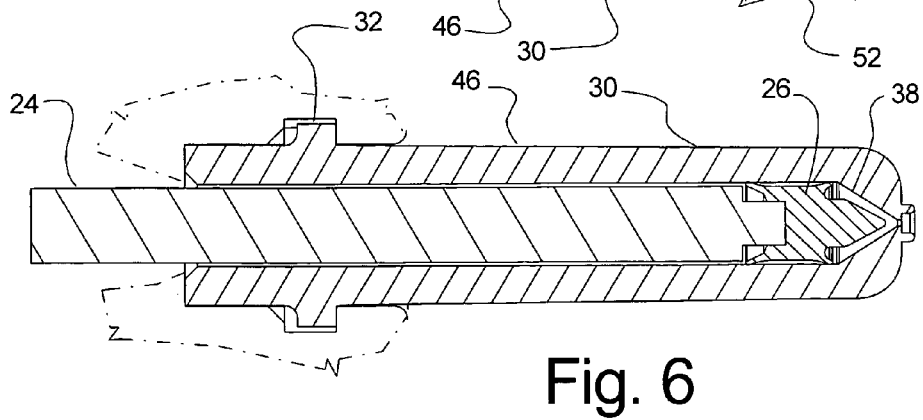
FIG. 6 illustrates the cooperation of the pluger and ampule at the end of the stroke or delivery cycle.
Figure 7:
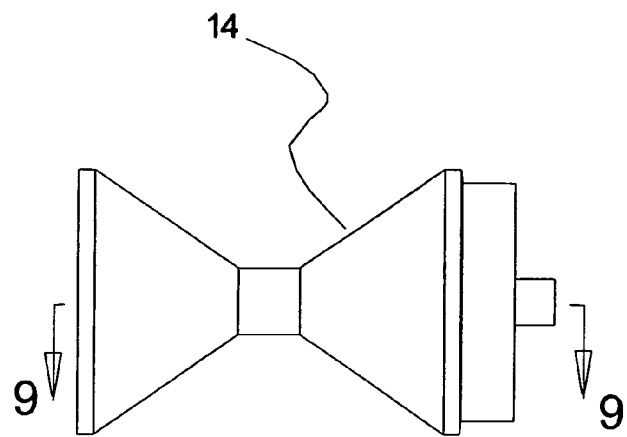
FIG. 7 is a side view of the hammer that is mounted between the spring and the push-rod.
Figure 8:
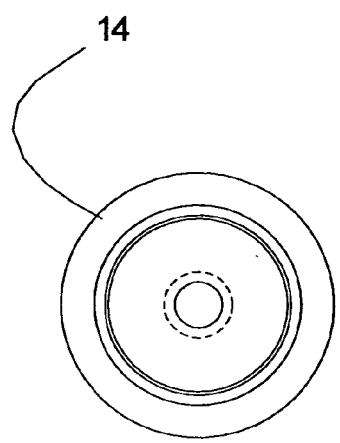
FIG. 8 is an end view of the hammer show in FIG. 7.
Figure 9:
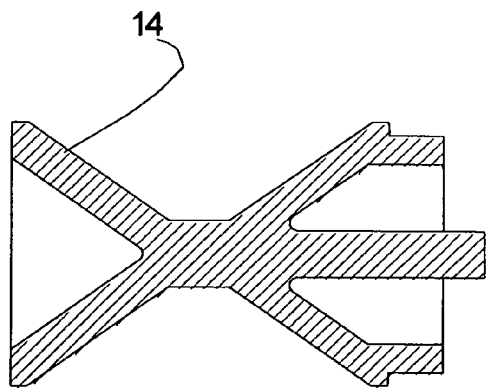
FIG. 9 is a sectional view taken from FIG. 7 in the direction indicated by the section arrows shown in FIG. 7.

Thus, FIGS. 3–6 illustrate the entire travel of the plunger 26 as driven by the spring 18 and hammer 14. Importantly, as illustrated in FIGS. 4 and 5, the deflection 42 of the ampule 30 that has been produced by the pressurization of the ampule 30 during travel of the plunger 26 through the ampule 30. In known devices, this deflection 42 causes a loss of pressure in the ampule 30, which results in an inadequate transfer of energy to the jet of medicament 34. However, the disclosed plunger 26 includes a concave rib 44 that is designed to open towards the nozzle 30. The concave rib 44 should be made of a flexible, yet strong material, such as polypropylene, rubber or other polymer.

In operation, as illustrated in FIGS. 3–6, the plunger 26 is driven through the aperture 28 by the force of the spring 18 pushing against the hammer 14. As the plunger 26 is driven through the elongated hollow body 46 of the ampule 30, the plunger 26 pushes the medicament 36 from the ampule 30 and through the nozzle 38. The elongated hollow body 46 of the ampule 30 include a first end 40 and a second end 50. Thus, the plunger 26 is pushed through the aperture 28, from the first end 40 towards the second end 50 of the amplule 30. The pressure within the aperture 28 of the ampule 30 increase as the plunger 26 is pressed against the medicament 36, causing the deflection 42 of the ampule 30. In order to maintain the pressure, and hence the required energy transfer to produce the jet of medicament 34, the concave rib 44 expands under the pressure, as indicated by the arrows 52 in FIG. 5. The expansion or flaring out of the concave rib 44 takes up or seals any fluid passages or bypasses that may be otherwise formed due to the expansion of the amplule 30.

Thus, from the accompanying illustrations, it will be understood that the plunger 26 extends about an axis 54 and may also include a first end 56 that terminates in a generally conical surface 58. Additionally, the plunger 26 includes a second end 60 and a mid-portion 61, located between the first end 56 and the second end 60. Still further, the plunger 26 will also include an external surface 62 that may be cylindrical or of any other suitable cross-section. The concave rib 44 extends about the axis 54, and expands towards the first end 56 of the plunger 26. In the illustrated example, the concave rib 44 extends over the conical surface 58 of the plunger and towards the first end 56 of the plunger 26. Still further, in the illustrated example, the concave rib 44 extends over a portion of the conical surface 58. The conical surface 58 cooperates with the nozzle 38 to push any remaining medicaments from the ampule 30.

Figures 10, 11:
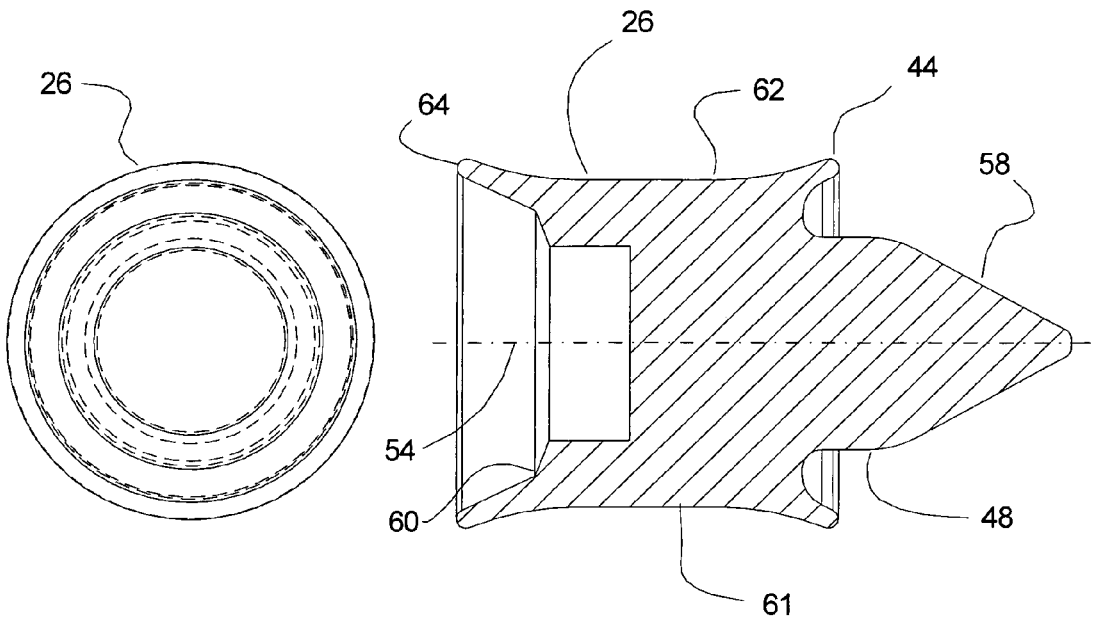
FIG. 10 is an end view of the example of the plunger.
FIG. 11 is a side, sectional view of the plunger.
Figure 12:
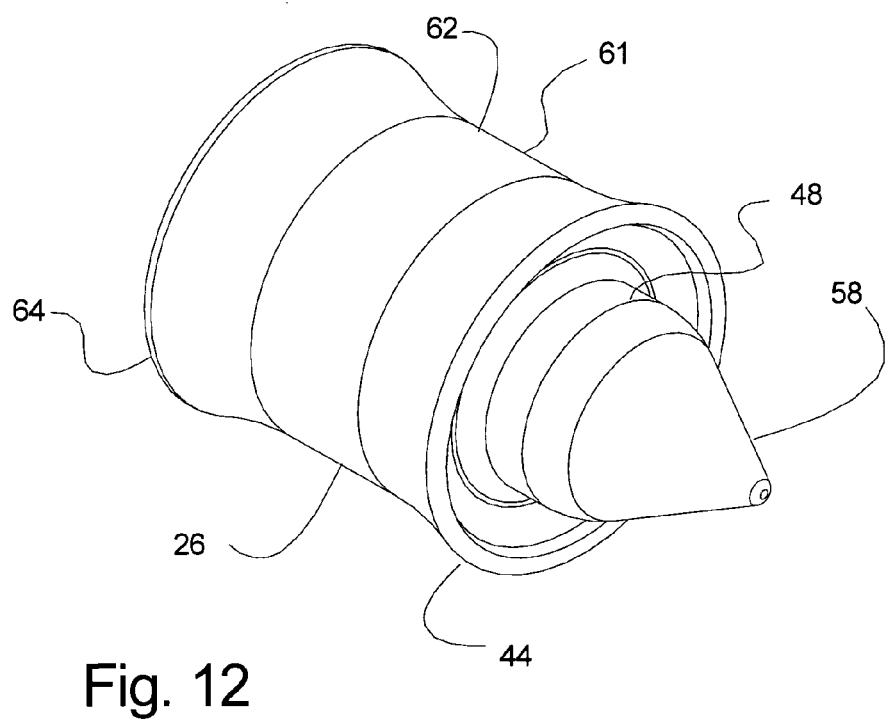
FIG. 12 is a perspective view of the plunger.

Turning now to FIGS. 10–12, it will be understood that it is contemplated that the plunger 26 may also include a second rib 64. The second rib 64 is positioned between the concave rib 44 and the second end 60 of the plunger 26. The second rib 64 cooperates with the concave rib 44 to stabilize the plunger 26 as it is driven through the ampule 30. The design of the concave rib 44 has been illustrated as being approximately conical in shape. This conical shape provides flexibility that allows the second rib 64 to accommodate the shape of the sidewalls 66 of the aperture 28. However, it is contemplated that the shape or cross-section of the second rib 64 may be one of many different shapes, and may not act as a seal, meaning that the rib is not continuous about the exterior surface of the body of the plunger 26.

Figure 13:
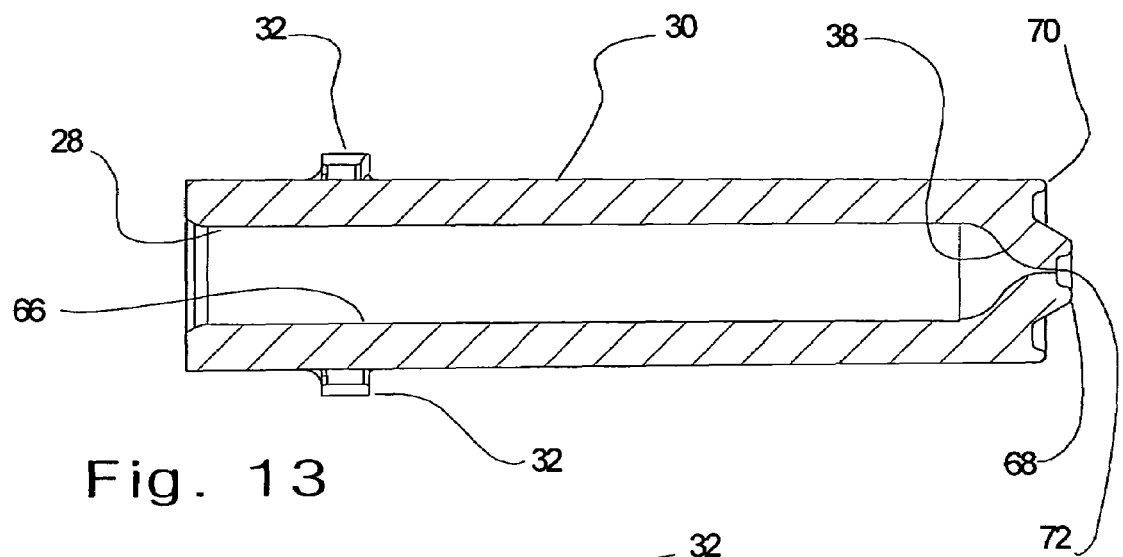
FIG. 13 is a side, sectional view of the vial or ampule.
Figure 14:
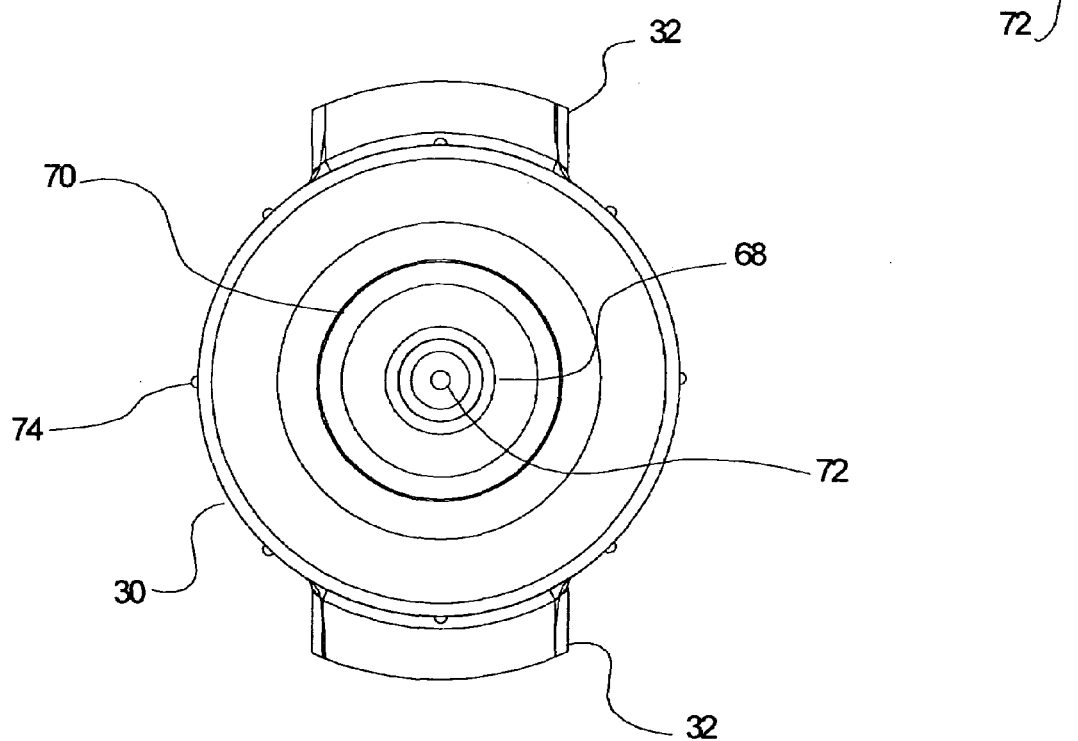
FIG. 14 is an end view of the vial or ampule, the view looking towards the nozzle.

FIGS. 13 and 14 provide greater detail of the amplule 30, and illustrate that it is contemplated that the nozzle 38 should be located within a raised annular portion 68, which in turn is located within a recessed annular portion 70. The recessed annular portion 70 cooperates with the raised annular portion to pull the skin tight, and retain this tightness, around the nozzle opening 72, so that the nozzle opening 72 is at a distance from the skin and the skin that is to be injected is pulled taut so as to avoid energy losses in the jet of medicament as the jet of medicament impacts the skin. In other words, by pulling the skin taut, one minimizes energy losses due to deflection of the skin. Still further, the bayonet connectors 32 are clearly visible from these figures, together with radially positioned stiffeners 74.

Thus it can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A piston driven needle-less injector system for holding a medicament and delivering a stream of the medicament through an area of skin on an animal, the system comprising:

A plunger, the plunger extending about an axis and having a first end, a second end, a mid-portion between the first end and the second end, and an external surface, the plunger including a concave rib that extends about the axis, expanding towards the first end of the plunger, the concave rib extending away from the external surface;

An unrestrained ampule, the ampule comprising an elongated hollow body made from a polypropylene material, the elongated hollow body having a first end and a second end, the first end of the elongated hollow body including a nozzle, and the second end of the hollow body including an aperture adapted for accepting the plunger, the aperture for accepting the plunger extending from the second end of the hollow body towards the first end of the hollow body and being in fluid communication with the nozzle, the aperture being sized such that the concave rib produces an sealing fit with the hollow body, while the external surface remains spaced apart from the hollow body, when the concave rib is inserted into the aperture of the hollow body, the concave rib cooperating with the elongated hollow body by expanding and sealing the aperture in response to a deflection in the hollow body, so that deflections in the hollow body caused by a pressure force created as the medicament driven from the hollow body by the plunger are sealed by the concave rib.

2. A system according to claim 1 wherein said plunger further comprises a second rib, the second rib being between the concave rib and the second end of the plunger.

3. A system according to claim 1, wherein said first end of said plunger is approximately conical in shape.

4. A system according to claim 3 wherein said plunger comprises a second rib extending from said external surface, the second rib being located between the concave rib and the second end of the plunger.

5. A system according to claim 1 wherein the first end of the plunger has been adapted for nesting within a substantial portion of said nozzle.

6. A system according to claim 1 wherein the polymer of said plunger is a polypropylene material, so that the plunger and the vial are made of the same material.

7. A piston driven needle-less injector system for holding a medicament and delivering a stream of the medicament through an area of skin on an animal, the system comprising:

A cylindrical plunger, the cylindrical plunger extending about an axis and having a first end that terminates with a generally conical surface, a second end, a mid-portion between the first end and the second end, and an external surface, the cylindrical plunger including a concave rib that extends about the axis, expanding away from the conical surface of the plunger and towards the first end of the plunger;

An ampule, the ampule comprising an elongated hollow body made from a polypropylene material, the elongated hollow body having a first end and a second end, the first end of the elongated hollow body including a nozzle, and the second end of the hollow body including an aperture adapted for accepting the plunger, the aperture being sized such that the concave rib produces an sealing fit with the hollow body, while the external surface remains spaced apart from the hollow body, when the concave rib is inserted into the aperture of the hollow body, the aperture for accepting the plunger extending from the second end of the hollow body towards the first end of the hollow body and being in fluid communication with the nozzle, the concave rib cooperating with the elongated hollow body by expanding and sealing the aperture in response to a deflection in the hollow body, so that deflections in the hollow body caused by a pressure force created as the medicament is driven from the hollow body by the plunger are sealed by the concave rib.

8. A system according to claim 7 wherein said plunger further comprises a second rib, the second rib being between the concave rib and the second end of the plunger.

9. A system according to claim 7, wherein said concave rib is approximately conical in shape.

10. A system according to claim 9 wherein said plunger comprises a second rib extending from said external surface, the second rib being generally conical and located between the concave rib and the second end of the plunger.

11. A system according to claim 7 wherein the first end of the plunger has been adapted for nesting within a substantial portion of said nozzle.

12. A method for preventing pressure losses in a piston driven needle-less injector system while delivering a medicament as a stream, the method comprising:

providing a plunger that is made from polypropylene, the plunger extending about an axis and having a first end, a second end, a mid-portion between the first end and the second end, and an external surface, the plunger including a concave rib that extends about the axis, expanding towards the first end of the plunger;

providing an ampule, the ampule comprising an elongated hollow body made from a polypropylene material, the elongated hollow body having a first end and a second end, the first end of the elongated hollow body including a nozzle, and the second end of the hollow body including an aperture adapted for accepting the plunger, the aperture being sized such that the concave rib produces an sealing fit with the hollow body, while the external surface remains spaced apart from the hollow body, when the concave rib is inserted into the aperture of the hollow body, the aperture for accepting the plunger extending from the second end of the hollow body towards the first end of the hollow body and being in fluid communication with the nozzle;

providing an amount of fluid medicament within the ampule, and placing the plunger into the hollow body so that the medicament is held between the plunger and the nozzle;

compressing the medicament by driving the plunger towards the nozzle, casing causing the concave rib to expand against the elongated hollow body and seal the aperture in response to a deflection in the hollow body caused by the compression of the medicament by moving of the plunger towards the nozzle, so that deflections in the hollow body caused by a pressure force created as the medicament is driven from the hollow body by the plunger are sealed by the concave rib.

13. A method according to claim 12 wherein said plunger further comprises a second rib, the second rib being between the concave rib and the second end of the plunger.

14. A method according to claim 12, wherein said first end of said plunger is approximately conical in shape.

15. A method according to claim 14 wherein said plunger comprises a second rib extending from said external surface, the second rib being located between the concave rib and the second end of the plunger.

16. A system according to claim 12 wherein the first end of the plunger has been adapted for nesting within a substantial portion of said nozzle.

* * * * *